United States Patent
Wei et al.

(10) Patent No.: US 12,377,040 B1
(45) Date of Patent: Aug. 5, 2025

(54) ***RHODOSORUS MARINUS* AND APPLICATION THEREOF IN PREPARING FACIAL MASKS**

(71) Applicant: Hainan Normal University, Hainan (CN)

(72) Inventors: Li Wei, Hainan (CN); Han Zhu, Hainan (CN); Li Zhang, Hainan (CN); Lishan Lan, Hainan (CN); Chunyun Lei, Hainan (CN); Hang Su, Hainan (CN)

(73) Assignee: Hainan Normal University, Haikou (CN)

( * ) Notice: Subject to any disclaimer, the term of this patent is extended or adjusted under 35 U.S.C. 154(b) by 0 days.

(21) Appl. No.: 18/961,323

(22) Filed: Nov. 26, 2024

(30) Foreign Application Priority Data

Apr. 14, 2024 (CN) .......................... 202410444569.0

(51) Int. Cl.
| | | |
|---|---|---|
| *A61K 8/9717* | (2017.01) | |
| *A61K 8/02* | (2006.01) | |
| *A61K 8/60* | (2006.01) | |
| *A61K 8/65* | (2006.01) | |
| *A61Q 19/08* | (2006.01) | |
| *C12N 1/12* | (2006.01) | |
| *C12P 21/06* | (2006.01) | |
| *C12R 1/89* | (2006.01) | |

(52) U.S. Cl.
CPC .......... *A61K 8/9717* (2017.08); *A61K 8/0212* (2013.01); *A61K 8/602* (2013.01); *A61K 8/65* (2013.01); *A61Q 19/08* (2013.01); *C12N 1/125* (2021.05); *C12P 21/06* (2013.01); *A61K 2800/522* (2013.01); *C12R 2001/89* (2021.05)

(58) Field of Classification Search
CPC .................................................... A61K 8/9717
See application file for complete search history.

(56) References Cited

FOREIGN PATENT DOCUMENTS

CN 114958948 A 8/2022

OTHER PUBLICATIONS

Basaca-Loya et al, Extraction and purification of B-phycoerythrin from the red microalga Rhodosorus marinus. Ciencias Marinas (2009), vol. 35, No. 4, pp. 359-368 (Year: 2009).*
"Review on extraction purification and biological activity of phycobiliprotein", Tangwei Zhang et al., Biotechnol. Journal, No. 1, pp. 9-13.
"The research progress of antioxidant and moisturizing active substance in seaweed", Yanyan Wu et al., Marine Sci.39, 138-142.

* cited by examiner

*Primary Examiner* — Qiuwen Mi

(57) ABSTRACT

The present disclosure relates to *Rhodosorus marinus* and an application thereof in preparing facial masks. *Rhodosorus marinus* ZS2001 has the following collection information: collection institution: China Center for Type Culture Collection (CCTCC); address of the collection institution: Wuhan University, No. 299 Bayi Road, Wuchang District, Wuhan City, Hubei Province; collection date: Oct. 30, 2023; collection number: CCTCC NO: M20232086; and collection name: *Rhodosorus marinus*.

1 Claim, 5 Drawing Sheets

*RHODOSORUS MARINUS* AND APPLICATION THEREOF IN PREPARING FACIAL MASKS

CROSS-REFERENCE TO RELATED APPLICATION

This application claims priority of Chinese Patent Application No. 202410444569.0, filed on Apr. 14, 2024, the entire contents of which are incorporated herein by reference.

TECHNICAL FIELD

The present disclosure relates to the field of marine *Rhodosorus marinus* cosmetics, and specifically to *Rhodosorus marinus* and an application thereof in preparing facial masks.

BACKGROUND

*Rhodosorus marinus*, classified into Rhodophyta, is a unicellular eukaryote, and contains phycobiliproteins, primarily including B-phycoerythrin, C-phycocyanin, and allophycocyanin. It is excellent not only in scavenging free radicals and inhibiting lipid peroxidation, but also in inhibiting inflammatory responses. According to the latest studies, the active peptide of *Rhodosorus marinus* may be effective in treating skin allergy, because it is rich in antioxidants that contribute to fighting against free radicals, reducing skin damage, and providing antioxidant protection for skin. Additionally, the active peptide can reinforce skin barriers and offer prolonged moisturizing effects, beneficial for dry skin to some extent. Studies have shown that active peptide can promote the generation of collagen, which helps to improve skin elasticity while reducing wrinkles and fine lines.

Conventional facial mask products are typically based on water, gel and emulsion, and contain some common skincare ingredients such as vitamins and antioxidants. However, these conventional facial masks often provide insufficient deep nourishment, especially for those who require additional moisturizing and anti-aging effects and prefer green skincare. The present disclosure provides *Rhodosorus marinus* and an application thereof in preparing facial masks.

SUMMARY

The present disclosure provides *Rhodosorus marinus* ZS2001, having the following collection information: collection institution: China Center for Type Culture Collection (CCTCC); address of the collection institution: Wuhan University, No. 299 Bayi Road, Wuchang District, Wuhan City, Hubei Province; collection date: Oct. 30, 2023; collection number: CCTCC NO: M20232086; and collection name: *Rhodosorus marinus*.

Another embodiment of the present disclosure provides a phycoerythrin. A preparation method for the phycoerythrin includes the following steps:
(1) taking fresh *Rhodosorus marinus* to undergo a first centrifugation, soaking the centrifuged *Rhodosorus marinus* in water, performing ultrasound on the soaked *Rhodosorus marinus*, followed by a second centrifugation to collect supernatant, and obtaining a crude phycoerythrin extract; and
(2) purifying the crude phycoerythrin extract obtained in step (1) once using a saturated ammonium sulfate method to obtain a preliminarily purified phycoerythrin.

In step (1), the first centrifugation is performed at a rotational speed of 5000-6000 rpm for a duration of 5-8 min; during the soaking in water, a mass/volume ratio of materials to liquid is 1:25-30, with a soaking time of 1-2 h; an ultrasound time is 10-15 min; and the second centrifugation is performed at a rotational speed of 8000-10000 rpm for a duration of 3-5 min.

The preliminarily purified phycoerythrin obtained in step (2) has a purity of 0.7 or more.

Another embodiment of the present disclosure provides a phycoerythrin. A preparation method for the phycoerythrin includes the following steps:
purifying the preliminarily purified phycoerythrin obtained in step (2) once more using the saturated ammonium sulfate method to obtain a secondary purified phycoerythrin.

The secondary purified phycoerythrin has a purity of 0.9 or more.

Another embodiment of the present disclosure provides an active peptide of *Rhodosorus marinus*. A preparation method for the active peptide of *Rhodosorus marinus* includes the following steps:
dissolving the phycoerythrin (preliminarily purified or secondary purified) in phosphate buffered saline (PBS), and adding an appropriate amount of neutral protease, followed by enzymolysis at 40-50° C. for 4-6 h to obtain an enzymatic hydrolysate, which is subjected to centrifugation, concentration, and freeze-drying sequentially to obtain the active peptide of *Rhodosorus marinus*.

The PBS is 0.05 mol/L with a pH of 6.5; and the amount of neutral protease is 2%-3% of a mass of the phycoerythrin. Food-grade neutral protease is preferably selected as the neutral protease.

Another embodiment of the present disclosure provides a facial mask of *Rhodosorus marinus*, a formulation thereof including the following components by mass percentage: 10% of *Rhodosorus marinus* extract, 3% of squalane, 0.3% of fragrance, 0.02% of disodium ethylenediamine tetraacetate (EDTA-2Na), 6% of glycerol, 2% of propylene glycol, 0.05% of collagen, 0.05% of xanthan gum, 0.1% of preservative, and 78.48% of water. The *Rhodosorus marinus* extract is selected from the foregoing phycoerythrin (preliminarily purified or secondary purified) and/or active peptide of *Rhodosorus marinus*.

Another embodiment of the present disclosure provides a preparation method for the foregoing facial mask of *Rhodosorus marinus*, including the following steps: mixing the xanthan gum and water according to the amount of formulation, followed by heating at 80° C. and stirring uniformly until white solids are absent; adding the glycerol, the propylene glycol, and EDTA-2Na, followed by stirring uniformly, stopping the heating, and cooling to 50° C. or below; adding the *Rhodosorus marinus* extract, the squalane, the collagen, the preservative, and the fragrance, followed by stirring uniformly, and emulsifying a mixture at room temperature for 10-15 min to obtain a facial mask essence; and using Tencel fabric as a sheet mask, and putting the same into the facial mask essence, followed by packaging to obtain the facial mask of *Rhodosorus marinus*.

Another embodiment of the present disclosure provides an application of the foregoing *Rhodosorus marinus* ZS2001 in preparing the phycoerythrin or the active peptide of *Rhodosorus marinus*.

Another embodiment of the present disclosure provides an application of the foregoing *Rhodosorus marinus* ZS2001 in preparing the facial mask of *Rhodosorus marinus*.

Another embodiment of the present disclosure provides an application of the foregoing phycoerythrin or active peptide of *Rhodosorus marinus* in preparing antioxidants.

Another embodiment of the present disclosure provides an application of the foregoing phycoerythrin or active peptide of *Rhodosorus marinus* in preparing daily cosmetics. The daily cosmetics are selected from facial masks, facial creams, and facial cleansers.

Compared with the prior art, the present disclosure has the following beneficial effects. The *Rhodosorus marinus* ZS2001 provided by the present disclosure represents a new type of algae. The extracts of this algae, including phycoerythrin and active peptide of *Rhodosorus marinus*, show significant antioxidant activity, and can be applied in preparing daily cosmetics such as facial masks.

DETAILED DESCRIPTION

Figure 1:
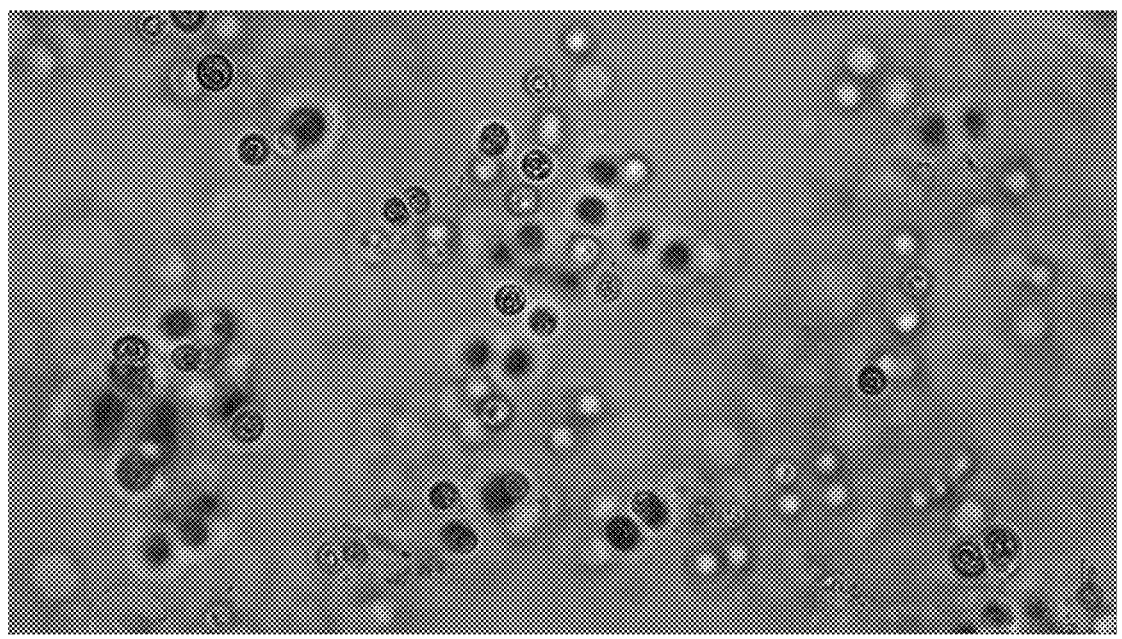
FIG. 1 is a diagram showing *Rhodosorus marinus* ZS2001 observed under a microscope according to the present disclosure.
Figure 2:
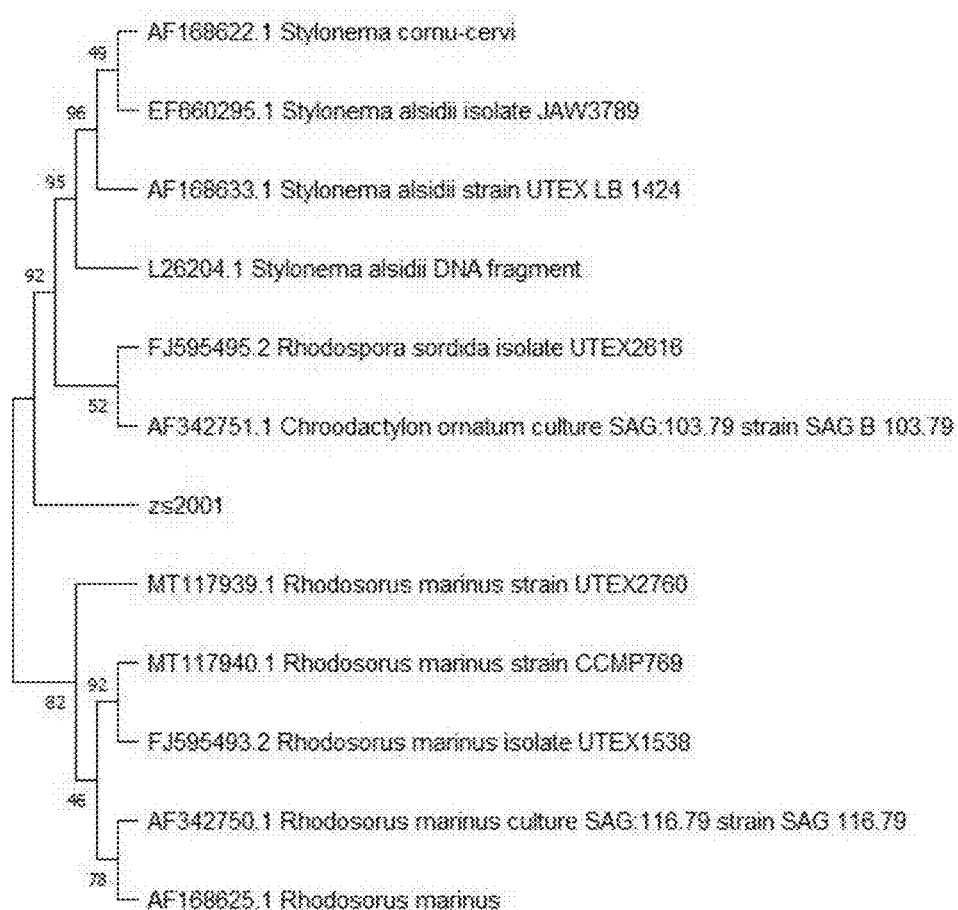
FIG. 2 is a phylogenetic tree analyzing the evolutionary position of *Rhodosorus marinus* ZS2001 according to the present disclosure.
Figure 3A:
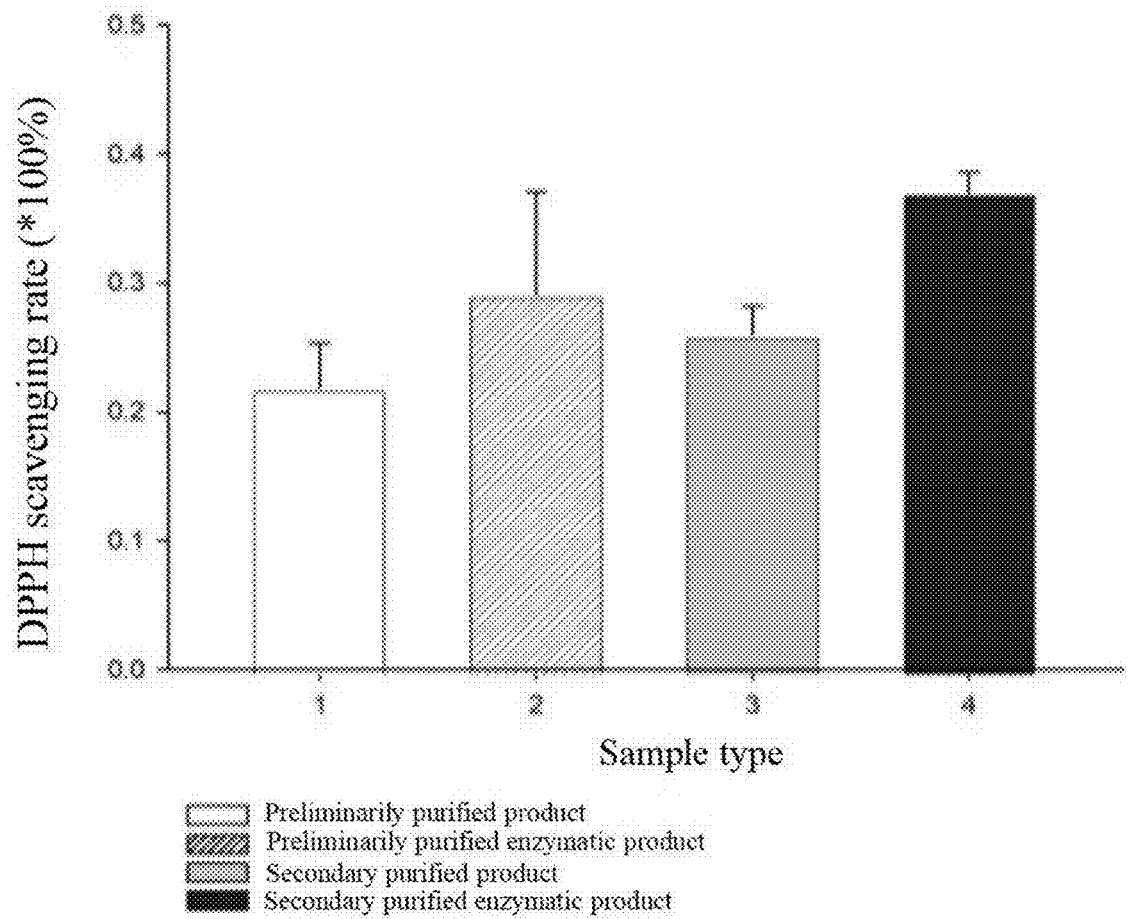
FIG. 3A is a diagram showing the determination of phycoerythrin and active peptide of *Rhodosorus marinus* in free radical scavenging activity.
Figure 3B:
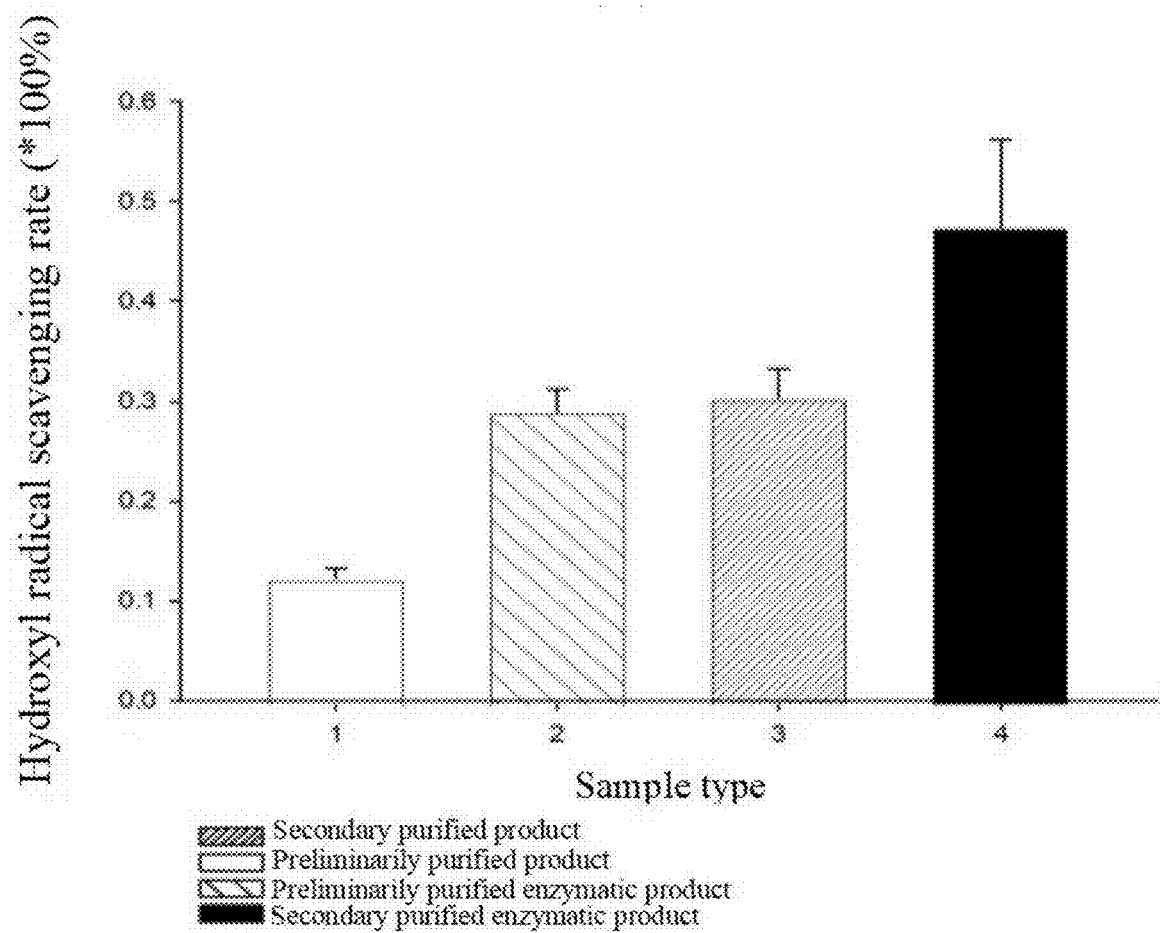
FIG. 3B is a diagram showing the determination of phycoerythrin and active peptide of *Rhodosorus marinus* in hydroxyl radical scavenging activity.
Figure 3C:
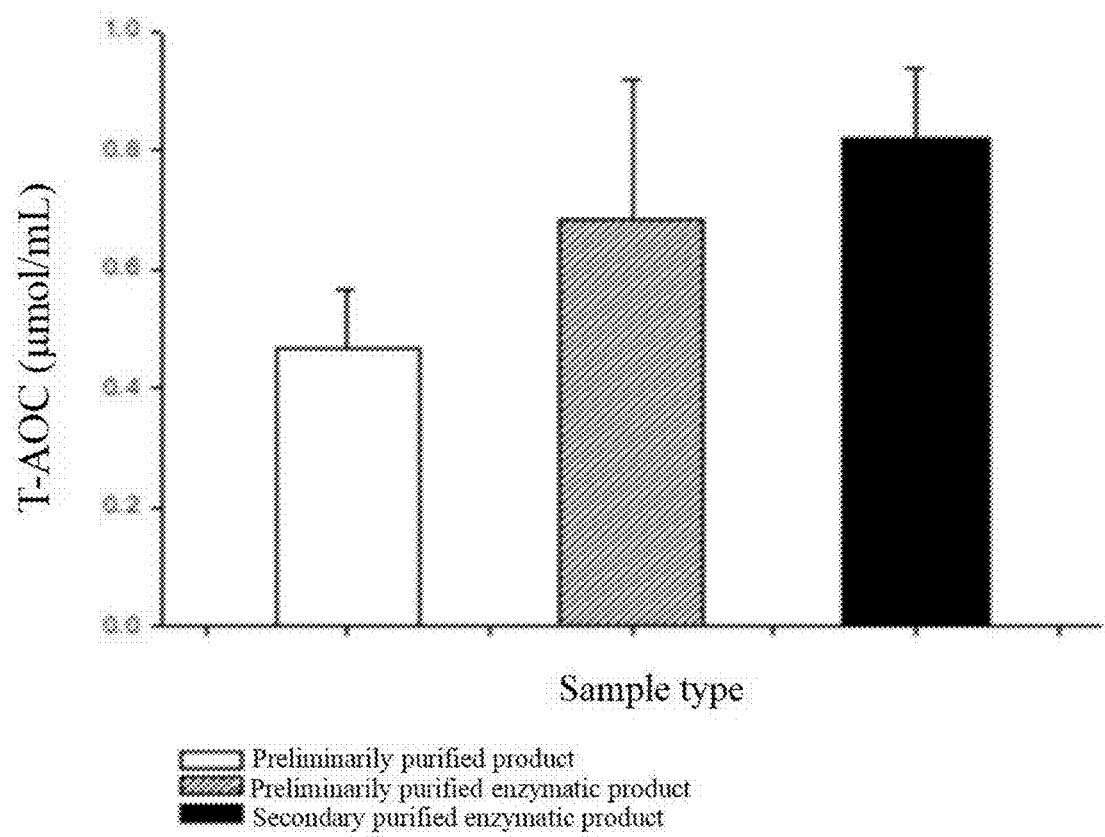
FIG. 3C is a diagram showing the determination of phycoerythrin and active peptide of *Rhodosorus marinus* in total antioxidant activity.

The present disclosure is described in detail by reference to the examples below. The following examples assist those skilled in the art in further understanding the present disclosure, but are not intended to limit the present disclosure in any form. It is to be noted that, for those ordinary skilled in the art, several adjustments and improvements may be made without departing from the conception of the present disclosure, all of which fall within the scope of protection of the present disclosure.

Example 1

(1) Fresh *Rhodosorus marinus* (200 g) was taken to undergo a first centrifugation (at 5000 rpm for 7 min), and the centrifuged *Rhodosorus marinus* was soaked in water (in a mass/volume ratio of material to liquid of 1:30) for 2 h. Ultrasound (at power of 500 W for 15 min) was performed on the soaked *Rhodosorus marinus*, followed by a second centrifugation (at 8000 rpm for 5 min) to collect supernatant, and a crude phycoerythrin extract was obtained (with a purity of 0.389).

(2) The crude phycoerythrin extract obtained in step (1) was purified once using a saturated ammonium sulfate method to obtain a preliminarily purified phycoerythrin (with a purity of 0.725, hereinafter referred to as Sample A).

(3) The preliminarily purified phycoerythrin obtained in step (2) was purified once more using the saturated ammonium sulfate method to obtain a secondary purified phycoerythrin (with a purity of 0.930, hereinafter referred to as Sample B).

In the present disclosure, an equation for calculating the purity of phycoerythrin=A565/A280, and a concentration of the phycoerythrin is measured by Bradford method. Purification of proteins using the saturated ammonium sulfate method (20%, 30%, 40%, 50%, 60%, and 70%) is a normal operation in this field. For example, at room temperature, 1.71 g of ammonium sulfate can be slowly added to 15 mL of the crude phycoerythrin extract, followed by gently and uniformly stirring to dissolve the phycoerythrin, leaving a mixture at 4° C. overnight. The next day, a table centrifuge (model Centrifuge 5425rR) can be employed to centrifuge the mixture at 10000 rpm for 10 min at room temperature, to separate precipitate and supernatant, and the precipitate is collected to obtain a preliminarily purified phycoerythrin.

Example 2

Phycoerythrin (preliminarily purified, 1.0 g) was dissolved in 0.05 mol/L of PBS with a pH of 6.5, and food-grade neutral protease (20 mg, Solarbio, with an enzyme activity of 50000 u/g) was added, followed by enzymolysis at 45° C. for 5 h to obtain an enzymatic hydrolysate, which was subjected to centrifugation, concentration, and freeze-drying sequentially to obtain an active peptide of *Rhodosorus marinus* (after preliminary purification and enzymolysis, hereinafter referred to as Sample C).

Example 3

Phycoerythrin (secondary purified, 1.0 g) was dissolved in 0.05 mol/L of PBS with a pH of 6.5, and food-grade neutral protease (30 mg, Solarbio, with an enzyme activity of 50000 u/g) was added, followed by enzymolysis at 50° C. for 4 h to obtain an enzymatic hydrolysate, which was subjected to centrifugation, concentration, and freeze-drying sequentially to obtain an active peptide of *Rhodosorus marinus* (after secondary purification and enzymolysis, hereinafter referred to as Sample D).

Example 4

0.05 g of xanthan gum was mixed with 78.48 mL of deionized water, followed by heating at 80° C. and stirring uniformly until there were no white solids. 6 g of glycerol, 2 g of propylene glycol, and 0.02 g of EDTA-2Na were added, followed by stirring uniformly. The heating was stopped to cool a mixture to 50° C. or below. 10 g of phycoerythrin (secondary purified), 3 g of squalane, 0.05 g of collagen, 0.1 g of preservative, and 0.3 g of fragrance were added, followed by stirring uniformly. A mixture was emulsified at room temperature for 10 min to obtain a facial mask essence. Tencel fabric was used as a sheet mask, and was put into the facial mask essence, followed by packaging to obtain a facial mask of *Rhodosorus marinus*.

Example 5

0.05 g of xanthan gum was mixed with 78.48 mL of deionized water, followed by heating at 80° C. and stirring uniformly until there were no white solids. 6 g of glycerol, 2 g of propylene glycol, and 0.02 g of EDTA-2Na were added, followed by stirring uniformly. The heating was stopped to cool a mixture to 50° C. or below. 10 g of active peptide of *Rhodosorus marinus* (after secondary purification and enzymolysis), 3 g of squalane, 0.05 g of collagen, 0.1 g of preservative, and 0.3 g of fragrance were added, followed by stirring uniformly. A mixture was emulsified at room temperature for 10 min to obtain a facial mask essence. Tencel fabric was used as a sheet mask, and was put into the facial mask essence, followed by packaging to obtain a facial mask of Rhodosorus marinus.

Example 6: determination of the antioxidant capacity (AOC) of phycoerythrin (Samples A and B) and active peptide of Rhodosorus marinus (Samples C and D)

In the field of cosmetics, the anti-aging property is typically characterized by the capability to scavenge 1,1-diphenyl-2-picrylhydrazyl (DPPH) radicals. DPPH radicals have single electrons and purple alcoholic solution, with a characteristic absorption at 515 nm. In the presence of antioxidants, DPPH radicals are scavenged. Within a certain range, the change in absorbance is proportional to the degree of radical scavenging. The capability of a sample to scavenge DPPH radicals can be reflected by the decrease degree of absorbance. The capability is represented by scavenging rate, and the higher the scavenging rate, the stronger the AOC. In this experiment, two types of DPPH radical scavenging capacity detection kits: Solaorbi and Beijing BoxBio AKAO020C are employed.

The DPPH radical scavenging rate $(DS\ \%) = (A\ \text{blank} - A\ \text{measurement} + A\ \text{control})/A\ \text{blank} \times 100\%$.

The test concentrations of Samples A-D are all 0.1 mg/mL. Vitamin C at a concentration of 1 mg/mL is selected as a positive control, with a DPPH radical scavenging rate of 99.7%.

Test Results (Average of Three Tests):

| Test sample | DPPH radical scavenging rate (%) |
|---|---|
| Sample A | 21.87% |
| Sample C | 29.13% |
| Sample B | 26% |
| Sample D | 37% |

In summary, after testing, the average DPPH radical scavenging rate of the preliminarily purified samples is 21.87%, and the average DPPH radical scavenging rate of the enzymatic products obtained by treating the preliminarily purified samples with neutral protease is 29.13%; and the average DPPH radical scavenging rate of the secondary purified samples is 26%, and the average DPPH radical scavenging rate of the enzymatic products obtained by treating the secondary purified samples with neutral protease is 37%.

The total antioxidant capacity (T-AOC) refers to the total antioxidant level of various antioxidant substances and antioxidant enzymes, such as enzymes, vitamin C, vitamin E, and carotenoids of antioxidants, protecting cells and organisms from oxidative stress damage caused by reactive oxygen species. The ferric reducing antioxidant power (FRAP) method is used to determine T-AOC, based on the principle that antioxidants under acidic conditions can reduce $Fe^{3+}$-TPTZ to a blue complex, $Fe^{2+}$-TPTZ with a characteristic absorption peak at 593 nm. The change in absorption value can reflect the reducing capacity of the sample to be tested, i.e., the T-AOC of the sample. In this experiment, Beijing BoxBio AKAO012C T-AOC detection kits are employed.

$T\text{-AOC}(\text{umol/mL}) = [x \times V\ \text{reaction}]/V\ \text{sample} = 34 \times x$ Test results: the test concentrations of samples A, C, and D are all 0.1 mg/mL. Those concentrations involves the following test steps: 40 μmol/mL of FeSO4 standard solution is diluted with distilled water to concentrations of 0.1, 0.05, 0.025, 0.0125, 0.00625, and 0.003125 μmol/mL, to establish a standard curve, and no additional positive control is set up. The unit of T-AOC is defined as: the T-AOC of a sample is expressed by the ion concentration of the standard solution required to achieve the same absorbance change ($\Delta A$).

| Test sample | T-AOC (μmol/mL) |
|---|---|
| Sample A | 0.468 |
| Sample C | 0.683 |
| Sample D | 0.820 |

In summary, after testing, the average T-AOC of the preliminarily purified samples is 0.468, and the average T-AOC of the enzymatic products obtained by treating the preliminarily purified samples with neutral protease is 0.683; and the average T-AOC of the enzymatic products obtained by treating the secondary purified samples with neutral protease is 0.820.

$H_2O_2/Fe^{2+}$ generates hydroxyl radicals through the Fenton reaction, and $Fe^{2+}$ in the phenanthroline-$Fe^{2+}$ aqueous solution is oxidized to $Fe^{3+}$, resulting in a decrease in absorbance value at 536 nm. The capability of the sample to scavenge hydroxyl radicals can be characterized by the inhibition degree of the decrease rate of absorbance value. In this experiment, Beijing BoxBio AKAO013C hydroxyl radical scavenging capacity detection kits are employed.

Hydroxyl radical scavenging rate $D\ \% = (A\ \text{measurement} - A\ \text{control})/(A\ \text{blank} - A\ \text{control}) = \Delta A\ \text{measurement}/\Delta A\ \text{blank} \times 100\%$ Test results: the test concentrations of samples A-D are all 0.1 mg/mL. Ascorbic acid (vitamin C) at a concentration of 1 mg/mL is selected as a positive control, with a hydroxyl radical scavenging rate of 90.5%.

| Test sample | Hydroxyl radical scavenging rate (%) |
|---|---|
| Sample A | 12.3% |
| Sample C | 29.0% |
| Sample B | 30.0% |
| Sample D | 47.4% |

In summary, after testing, the average hydroxyl radical scavenging rate of the preliminarily purified samples is 12.3%, and the average hydroxyl radical scavenging rate of the enzymatic products obtained by treating the preliminarily purified samples with neutral protease is 29.0%; and the average hydroxyl radical scavenging rate of the secondary purified samples is 30.0%, and the average hydroxyl radical scavenging rate of the enzymatic products obtained by treating the secondary purified samples with neutral protease is 47.4%.

Specific examples of the present disclosure are described above. It is to be understood that the present disclosure is not limited to the particular embodiment described above, and those skilled in the field may make various deformations or modifications within the scope of the claims, which do not affect the essential contents of the present disclosure.

The invention claimed is:
1. A method for preparing phycoerythrin, comprising the following steps:
 (1) taking fresh *Rhodosorus marinus* ZS2001 to undergo a first centrifugation at 5000-6000 rpm for 5-8 minutes, soaking the centrifuged *Rhodosorus marinus* ZS2001 in water for 1-2 h, performing ultrasound on the soaked *Rhodosorus marinus* ZS2001, followed by a second centrifugation at 8,000-10,000 rpm for 3-5 min to collect supernatant, and obtaining a crude phycoerythrin extract; wherein the *Rhodosorus marinus* ZS2001 has the following collection information: collection institution: China Center for Type Culture Collection (CCTCC); address of the collection institution: Wuhan University, No. 299 Bayi Road, Wuchang District, Wuhan City, Hubei Province; collection date: Oct. 30, 2023; collection number: CCTCC NO: M20232086; and collection name: *Rhodosorus marinus*; and
 (2) purifying the crude phycoerythrin extract obtained in step (1) once using a saturated ammonium sulfate method to obtain a preliminarily purified phycoerythrin with a purity of 0.7 or more, and
 purifying the preliminarily purified phycoerythrin obtained in step (2) once more using the saturated ammonium sulfate method to obtain a secondary purified phycoerythrin with a purity of 0.9 or more.

\* \* \* \* \*